United States Patent
Park et al.

(10) Patent No.: US 12,186,303 B2
(45) Date of Patent: *Jan. 7, 2025

(54) FEED ADDITIVE FOR CATTLE COMPRISING N-ACETYL-L-TRYPTOPHAN AS ACTIVE INGREDIENT

(71) Applicant: CJ CHEILJEDANG CORPORATION, Seoul (KR)

(72) Inventors: Jin Seung Park, Seoul (KR); Jin Woo Jeon, Seoul (KR); Jun Ok Moon, Seoul (KR); Joo Young Lee, Seoul (KR); Hong-Gu Lee, Seoul (KR); Jae-Sung Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 660 days.

This patent is subject to a terminal disclaimer.

(21) Appl. No.: 17/287,356

(22) PCT Filed: Nov. 12, 2019

(86) PCT No.: PCT/KR2019/015334
§ 371 (c)(1),
(2) Date: Apr. 21, 2021

(87) PCT Pub. No.: WO2020/101322
PCT Pub. Date: May 22, 2020

(65) Prior Publication Data
US 2021/0379015 A1 Dec. 9, 2021

(30) Foreign Application Priority Data

Nov. 12, 2018 (KR) ........................ 10-2018-0138459

(51) Int. Cl.
| | |
|---|---|
| A61K 31/405 | (2006.01) |
| A23K 20/142 | (2016.01) |
| A23K 50/10 | (2016.01) |
| A61K 9/00 | (2006.01) |
| A61P 3/02 | (2006.01) |

(52) U.S. Cl.
CPC .......... *A61K 31/405* (2013.01); *A23K 20/142* (2016.05); *A23K 50/10* (2016.05); *A61K 9/0056* (2013.01); *A61P 3/02* (2018.01)

(58) Field of Classification Search
CPC .............. A61K 31/405; A61K 9/0056; A23K 20/142; A23K 50/10; A61P 3/02; A23V 2002/00
See application file for complete search history.

(56) References Cited

U.S. PATENT DOCUMENTS

2008/0214649 A1 9/2008 Yu et al.

FOREIGN PATENT DOCUMENTS

| CA | 2731281 A1 | * 12/2010 | ........... A23K 20/142 |
|---|---|---|---|
| CN | 1695483 A | 11/2005 | |
| JP | 61-247342 A | 11/1986 | |
| JP | 2-273145 A | 11/1990 | |
| KR | 10-0165692 B1 | 9/1998 | |
| KR | 10-2012-0036787 A | 4/2012 | |
| KR | 10-2016-0140463 A | 12/2016 | |
| KR | 10-2017-0017592 A | 2/2017 | |
| KR | 10-2018-0017818 A | 2/2018 | |
| KR | 10-2018-0106173 A | 10/2018 | |

OTHER PUBLICATIONS

Fujita et al. Additive for Livestock Feed and Feed Composition for Livestock. J. Nutr. Sci. Vitaminol., 1980, 26, 381-388. (Year: 1980).*
Wagner, Effects of Cold Stress on Cattle Performance and Management Factors to Reduce Cold Stress and Improve Performance, The Bovine Practitioner, 1988, 23, p. 88-93). (Year: 1988).*
West, Effects of Heat-Stress on Production in Dairy Cattle, J. Dairy Sci., 86, 2131-2144. (Year: 2003).*
Cao Hanwen, "Cold stress in yaks and its prevention and treatment," *Science and Technology Guide No. 31*, p. 107 (2017).
Sutoh et al., "Effects of intravenous tryptophan infusion on thermoregulation in steers exposed to acute heat stress," *Animal Science Journal* 89:777-783 (2018).
Fujita et al., "Utilization of N-Acetyl-$_L$-Tryptophan Given Intravenously to Unrestrained Adult Rats," *J. Nutr. Sci. Vitaminol.* 26:381-388 (1980).
Subuh et al., "Effect of heat or formaldehyde treatment on the rumen degradability and intestinal tract apparent digestibility of protein in soya-bean meal and in rapeseed meals of different glucosinolate content," *Animal Feed Science Technology* 57:256-265 (1996).
Langner et al., "Absorption Studies on Tryptophan and Acetyltryptophan," *J. Biol. Chem.* 223:583-588 (1956).

* cited by examiner

*Primary Examiner* — Matthew P Coughlin
*Assistant Examiner* — Meghan C Heasley
(74) *Attorney, Agent, or Firm* — Morgan, Lewis & Bockius LLP

(57) ABSTRACT

Provided are a feed additive composition for cattle including N-acetyl-L-tryptophan (NALT) as an active ingredient, and more particularly, a feed additive composition including N-acetyl-L-tryptophan as an active ingredient for reducing temperature stress of cattle, increasing average daily gain of cattle, and increasing feed intake of cattle; a feed including the feed additive composition for cattle; and methods of reducing temperature stress of cattle, increasing average daily gain of cattle, and increasing feed intake of cattle, the methods including feeding the cattle with the feed additive composition or feed for cattle including N-acetyl-L-tryptophan as an active ingredient.

5 Claims, No Drawings

FEED ADDITIVE FOR CATTLE COMPRISING N-ACETYL-L-TRYPTOPHAN AS ACTIVE INGREDIENT

TECHNICAL FIELD

The present disclosure relates to a feed additive composition for cattle including N-acetyl-L-tryptophan (NALT) as an active ingredient, and more particularly, to a feed additive composition including N-acetyl-L-tryptophan as an active ingredient for reducing temperature stress of cattle, increasing average daily gain of cattle, and increasing feed intake of cattle; a feed including the feed additive composition for cattle; and methods of reducing temperature stress of cattle, increasing average daily gain of cattle, and increasing feed intake of cattle, the methods including feeding the cattle with the feed additive composition or feed for cattle including N-acetyl-L-tryptophan as an active ingredient.

BACKGROUND ART

A thermal environment is very important compared to other environments since it directly affects homeostasis of cattle, a homoiothermic animal. The thermal environment for cattle means temperature, wind speed, solar radiation energy, relative humidity, heat production, materials and conditions of barn floors, insulation degrees of roofs, breeding density, and the like. Among these, the most important factor is temperature, according to reports from the National Institute of Animal Science, and a lower critical temperature for production of cattle, e.g., Korean native cattle, is known to be −10° C.

In a known optimal temperature range for cattle, heat production is almost constantly maintained at a low level, and productivity is almost constantly maintained at a high level. In contrast, the more the temperature deviates from the optimal temperature range, the more the productivity decreases. At a temperature outside of a critical temperature range for a production environment, productivity significantly decreases. Under the influence of global warming, climates in the temperate zones are becoming more polarized, resulting in hotter summers and colder winders. For reasons such as this, declines in productivity of ruminant animals are expected to accelerate under low-temperature environments in winter and under high-temperature environments in summer.

L-Tryptophan is one of essential amino acids (EAAs) nutritionally important in ruminant animals and is an essential component of protein synthesis. In general, L-tryptophan has a critical role in metabolism, physiological response, growth, and organ development. L-Tryptophan deficiency may adversely affect feed intake and growth performance. Meanwhile, since productivity of cattle declines under temperature stress conditions, e.g., cold and heat stress conditions, L-tryptophan, as an essential amino acid, needs to be supplemented to minimize declines in productivity.

When ruminant animals are supplemented with L-tryptophan, L-tryptophan is used in rumen microbes, resulting in an increase in microbial protein synthesis. However, as a result, ammonia produced in large quantities cannot be used, and efficiency of feed protein decreases. Thus, there is a need to feed L-tryptophan in the form of a rumen-bypass amino acid that is not degraded by microbes in the rumen but degraded and absorbed in the small intestine of ruminant animals. In general, in order to protect feed proteins from microbes in the rumen, various physiochemical treatment methods such as heat treatment, formaldehyde treatment (Subuh et al., *Animal Feed Science and Technology*, Vol. 57(3), 257-265), tannin treatment, ethanol treatment, and lignosulfonate treatment, and methods of coating the surface with a mixture of a fatty acid and pH sensitive polymer or with a mixture of an unsaturated fatty acid and a mineral have been studied.

DESCRIPTION OF EMBODIMENTS

Technical Problem

As a result of intensive efforts to develop feed additives for minimizing declines in productivity of cattle, the present inventors have found that by feeding N-acetyl-L-tryptophan, which has a conjugate form of acetate and L-tryptophan, temperature stress of cattle is reduced and average daily gain and feed intake of the cattle increased, thereby completing the present disclosure.

Solution to Problem

An object of the present disclosure is to provide a feed additive composition for cattle comprising N-acetyl-L-tryptophan as an active ingredient.

Another object of the present disclosure is to provide a feed comprising the feed additive composition for cattle.

Another object of the present disclosure is to provide methods of reducing temperature stress of cattle, increasing average daily gain of cattle, and increasing feed intake of cattle, the methods comprising feeding the cattle with the feed additive composition or feed comprising N-acetyl-L-tryptophan as an active ingredient.

Advantageous Effects of Disclosure

N-Acetyl-L-tryptophan (NALT) according to the present disclosure reduces temperature stress of cattle and increases average daily gain and feed intake of cattle, and thus it may be effectively used in a feed additive composition or a feed as an active ingredient.

BEST MODE

Hereinafter, the present disclosure will be described in detail. Meanwhile, each description and embodiment disclosed in the present disclosure may be applied herein to different descriptions and embodiments. In other words, all combinations of various components disclosed in the present disclosure are included within the scope of the present invention. Furthermore, the scope of the present disclosure should not be limited by the detailed description provided below.

An aspect of the present disclosure to achieve the above-described objects provides a feed additive composition for cattle comprising N-acetyl-L-tryptophan (NALT) as an active ingredient.

Specifically, the feed additive composition for cattle of the present disclosure may include N-acetyl-L-tryptophan or a salt thereof.

As used herein, the term "N-acetyl-L-tryptophan (NALT)" refers to a compound having a structure represented by Formula 1 below. Although N-acetyl-L-tryptophan is known to have various properties, such as therapeutic effects on the brain, spinal cord, and nerve damage and preventive effects on oxidation of proteins together with magnesium sulfate, effects of a feed including NALT on reducing temperature stress of cattle and increasing average daily gain and feed intake of cattle have not been reported and were first identified by the present inventors.

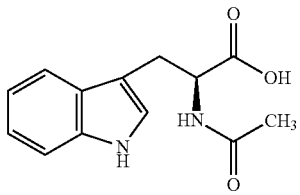 [SMILES: CC(=O)N[C@@H](Cc1c[nH]c2ccccc12)C(=O)O]

In view of the objects of the present disclosure, N-acetyl-L-tryptophan may be used without limitation as to sources thereof, and preparation of N-acetyl-L-tryptophan may be performed using any method well known in the art.

The term "L-tryptophan" is one of essential amino acids (EAAs) nutritionally important in ruminant animals and is an essential component of protein synthesis. Metabolites of L-tryptophan may allow organs to maintain homeostasis by regulating metabolism of nutrients and affect growth, development, reproduction, and health of animals. In addition, L-tryptophan, as a precursor of serotonin, which acts as a neurotransmitter, may relieve stress by regulating emotional behavior after passing through the blood-brain barrier. Also, as a precursor of melatonin and niacin, L-tryptophan is known to have antioxidant effects; promote secretion of cholecystokinin (CCK), which is a gastrointestinal hormone in the small intestine; and increase starch digestibility by secreting and activating pancreas α-amylase.

In the present disclosure, the N-acetyl-L-tryptophan may be rumen-protected. As used herein, the term "rumen-protected" means that nutrients are processed to be degraded and absorbed in the small intestine without being degraded in a ruminant stomach by microbial enzymes and is also referred to as rumen-bypass. The term "ruminant stomach" refers to a special alimentary canal found in some animals of the order Artiodactyla and is divided into four compartments for so-called rumination, i.e., rumen, reticulum, omasum, and abomasum. A process of regurgitating ingesta and rechewing the regurgitated ingesta for further breakdown thereof is called rumination, and a stomach enabling this process is the ruminant stomach. Since microbes live in the ruminant stomach, ruminant animals have the ability to digest plant cellulose, which is generally indigestible in other animals, to produce energy.

The N-acetyl-L-tryptophan of the present disclosure, having a conjugate form of acetate and L-tryptophan, is rumen-protected such that L-tryptophan is absorbed in the small intestine without being degraded by microbial enzymes in the ruminant stomach.

An amount of N-acetyl-L-tryptophan according to the present disclosure may be determined by one or ordinary skill in the art in consideration of a target animal, species and body weight of the target animal, feeding time, type of a feed, a purpose of feeding, and the like. Specifically, the amount of N-acetyl-L-tryptophan may be in the range of 0.01% (w/w) to 3.0% (w/w), 0.01% (w/w) to 2.0% (w/w), 0.01% (w/w) to 0.1% (w/w), 0.05% (w/w) to 3.0% (w/w), 0.05% (w/w) to 2.0% (w/w), or 0.05% (w/w) to 1.5% (w/w), more specifically 0.05% (w/w) to 1.0% (w/w), based on a total dry weight of the feed, without being limited thereto.

As used herein, the term "cattle" refers to bulls, cows, steers, or the like raised as livestock. As used herein, the term "beef cattle" refers to cattle raised for meat production among those raised as livestock. In the present disclosure, the beef cattle are cattle used for meat production and are included in the scope of the present disclosure regardless of breed, gender, or the like. More specifically, the beef cattle may be Korean native cattle, but are not limited thereto.

As used herein, the term "feed additive" refers to a substance added to a feed for the purpose of enhancing productivity or overall health of target subjects or for a particular use, but is not limited thereto. In addition, the feed additive may be an auxiliary feed under the Control of Livestock and Fish Feed Act.

The feed additive composition of the present disclosure may further include nucleotides, amino acids, calcium, phosphoric acid, and organic acids for enhancement of productivity or overall health of target subjects, in addition to N-acetyl-L-tryptophan or a salt thereof, but is not limited thereto.

As used herein, the term "salt" refers to a substance consisting of a cation and an anion that are bound by electrostatic attraction, and may generally be a metal salt, a salt with an organic base, a salt with an inorganic acid, a salt with an organic acid, a salt with an amino acid, or the like. For example, the metal salt may be an alkali metal salt (e.g., a sodium salt and a potassium salt), an alkaline earth metal salt (e.g., a calcium salt, a magnesium salt, and a barium salt), an aluminum salt, or the like; the salt with an organic base may be a salt with triethylamine, pyridine, picoline, 2,6-lutidine, ethanolamine, diethanolamine, triethanolamine, cyclohexylamine, dicyclohexylamine, N,N-dibenzylethylenediamine, or the like; the salt with an inorganic acid may be a salt with hydrochloric acid, hydrobromic acid, nitric acid, sulfuric acid, phosphoric acid, or the like; the salt with an organic acid may be a salt with formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, or the like; and the salt with the amino acid may be a salt with a basic or acidic amino acid, wherein the salt with an basic amino acid may be a salt with arginine, lysine, ornithine, or the like, and the salt with an acidic amino acid may be a salt with aspartic acid, glutamic acid, or the like.

In the present disclosure, the feed additive composition may be for reducing temperature stress. The feed additive composition may be a feed additive composition for beef cattle for reducing temperature stress.

As used herein, the term "temperature stress" refers to a decline in productivity of cattle in accordance with temperature changes, specifically a decline in productivity of cattle at a temperature outside of an optimal temperature range or due to a sudden temperature change, and may be cold stress or heat stress, without being limited thereto. Specifically, the cold stress may be stress caused at a temperature below the optimal temperature range, at a temperature below a lower critical temperature, or due to a sudden temperature decrease, and the heat stress may be stress caused at a temperature above the optimal temperature range, at a temperature above a higher critical temperature, or due to a sudden temperature increase, without being limited thereto. The temperature causing cold stress may be a temperature below +10° C. or a temperature of −50° C. to +10° C., −40° C. to +10° C., −30° C. to +10° C., −20° C. to +10° C., −10° C. to +10° C., or −10° C. to 0° C., but is not limited thereto. The temperature causing heat stress may be a temperature above 10° C., 15° C., or 20° C. or a temperature of 10° C. to 50° C., 15° C. to 50° C., 20° C. to 50° C., 30° C. to 50° C., 10° C. to 40° C., 15° C. to 40° C., 20° C. to 40° C., 30° C. to 40° C., 15° C. to 35° C., or 20° C. to 35° C., but is not limited thereto. The reduction of temperature stress may be evaluated based on increases in average daily gain and feed intake of cattle, without being limited thereto.

According to a report of the National Livestock Research Institute, an optimal temperature range and critical temperatures of Korean native cattle are as shown in Table 1. The lower critical temperature for breeding the Korean native cattle is known to be −10° C.

TABLE 1

Optimal temperature range and critical temperature of Korean native cattle

| Item | | Optimal temperature range (° C.) | Critical temperature (° C.) | |
|---|---|---|---|---|
| | | | Lower | Higher |
| Korean native cattle | Calf | 13-25 | −5 | 30 |
| | Growing calf | 4-20 | 10 | 30 |
| | Beef cattle | 10-20 | −10 | 30 |
| | Breeding cattle | 0-20 | −10 | 32 |

In a specific embodiment of the present disclosure, increases in average daily gain and increases in feed intake were identified by exposing cattle, e.g., beef cattle, to a temperature stress environment. Under cold stress conditions, an average temperature during an adaptation period (days 0-6) was 4.3° C., average temperatures during the experiment period were in the range of −6.2° C. to 4.2° C., and an average temperature of the entire experiment period (days 7-48) was −1.0° C. The average temperature of the experiment period was maintained at a lower level than that of the adaptation period (Table 4).

Under heat stress conditions, temperature was indicated using a temperature—humidity index (THI), which is a reference index of heat stress. The average THI was over 80 during the first three weeks, and the average THI was over 72 during the next four weeks (Table 10).

In the present disclosure, the feed additive composition may be for increasing average daily gain. The feed additive composition may be a feed additive composition for beef cattle for increasing average daily gain. The feed additive composition may be a feed additive composition for average daily gain (average daily weight gain) of beef cattle under heat or cold stress conditions. Specifically, the feed additive composition may be a feed additive composition for increasing average daily gain of beef cattle having a feed conversion ratio (value obtained by dividing average daily gain by feed intake) of 3 to 10. More specifically, the feed additive composition may be a feed additive composition for increasing average daily gain of beef cattle having a feed conversion ratio of 3 to 10 under heat or cold stress conditions. Specifically, the feed additive composition may be a feed additive composition for increasing average daily gain having a lower feed conversion ratio than beef cattle not fed with NALT by 50% to 80%. More specifically, the feed additive composition may be a feed additive composition for increasing average daily gain of beef cattle having a lower feed conversion ratio than beef cattle not fed with NALT by 50% to 80% under heat or cold stress conditions.

In a specific embodiment of the present disclosure, when the cattle were fed with the feed additive composition including NALT as an active ingredient of the present disclosure under the cold stress conditions, no statistically significant difference was observed between a total weight change of the NALT-treated group and that of the control. However, as a result of comparing the average daily gain (ADG) from the starting day of the experiment (week 0) to the mid-point of the experiment (week 4) with the average daily gain (ADG) from the mid-point of the experiment (week 4) to the final day of the experiment (week 7), statistically significant differences were observed in the average daily gain (ADG) of 0.753 (p=0.0301) and 0.766 (p=0.0003) in the NALT-treated group when compared with the control. (Table 5).

In a specific embodiment of the present disclosure, when the cattle were fed with the feed additive composition including NALT as an active ingredient of the present disclosure under heat stress conditions, effects on increasing weight gains were observed in the NALT-treated group compared with the control. In particular, it was confirmed that the average daily gain of the NALT-treated group was significantly increased compared to the average daily gain of the control during a period where the THI is about 80, i.e., under heat stress conditions (Table 11).

When the cattle were fed with the feed additive composition including NALT as an active ingredient of the present disclosure in a temperature stress environment, the feed conversion ratio, which is a value obtained by dividing average daily gain by feed intake, may be in the range of 1 to 13, 1 to 10, 1 to 8, 1 to 6, 1 to 5, 2 to 10, 2 to 8, 2 to 6, 2 to 5, 3 to 10, 3 to 8, 3 to 6, or 3 to 5. Meanwhile, based thereon, when the cattle were fed with the feed additive composition including NALT as an active ingredient of the present disclosure in a temperature stress environment, the feed conversion ratio was decreased by 40% to 80%, 40% to 70%, 50% to 80%, 50% to 70%, or 60% to 70% compared with beef cattle not fed with NALT.

In the present disclosure, the feed additive composition may be for increasing feed intake of cattle. The feed additive composition may be a feed additive composition for beef cattle for increasing feed intake. The feed additive composition may be a feed additive composition for increasing feed intake of beef cattle under heat or cold stress conditions. Specifically, the feed additive composition may be a feed additive composition for beef cattle for increasing feed intake thereof by at least 3% to 8% compared to those of beef cattle not fed with NALT under heat or cold stress conditions.

In a specific embodiment of the present disclosure, when the cattle were fed with the feed additive composition including NALT as an active ingredient of the present disclosure under cold stress conditions, no statistically significant difference (p=0.0883) was observed between feed intake of the NALT-treated group during the adaptation period (days 0-6) and that of the control during the adaptation period. In addition, although no statistically significant difference was observed between feed intake of the NALT-treated group during the experiment period of days 7-41 and that of the control during the same experiment period, the feed intake of the NALT-treated group during the experiment period of days 42-48 was increased by about 1.02 kg compared to the feed intake of the control during the same experiment period, indicating a statistically significant difference therebetween (p=0.0384). In addition, as a result of calculating average feed intake per head during the entire experiment period (days 7-48), the NALT-treated group exhibited feed intake of 9.86 kg/day/head on average, which was higher than that of the control (9.43 kg/day/head) by about 4.6%, indicating a statistically significant difference therebetween (p=0.0119) (Table 6).

In a specific embodiment of the present disclosure, when the cattle were fed with the feed additive composition including NALT as an active ingredient of the present disclosure under heat stress conditions, average feed intake of the control was 13.38 kg/day, and that of the NALT-treated group was 13.62 kg/day, indicating no statistically significant difference therebetween. However, it was confirmed that the feed intake of the NALT-treated group was significantly increased compared to the feed intake of the control at a THI of 80 or more (Table 12). Based thereon, when the cattle were fed with the feed additive composition including NALT as an active ingredient of the present disclosure in a temperature stress environment, the feed intake may be increased by at least 2% to 10%, 2% to 8%, 4% to 10%, 3% to 8%, 4% to 10%, 3% to 7%, or 4% to 7%.

In the present disclosure, the feed intake of beef cattle may be calculated by measuring a total amount of feed offered and an amount left over, but is not limited thereto.

In the present disclosure, the feed additive composition may be for reducing expression of proteins related to fat metabolism in loin tissue. The feed additive composition may be a feed additive composition for beef cattle to reduce expression of proteins related to fat metabolism in loin tissue. The feed additive composition may be a feed additive composition for reducing expression of proteins related to fat metabolism in loin tissue of beef cattle under heat or cold stress conditions. Specifically, the feed additive composition may be a feed additive composition for reducing expression of genes (at least one of PPARr, CEBPa, and FABP4) related to fat metabolism in loin tissue of cattle. More specifically, the feed additive composition may be a feed additive composition for reducing expression of genes (at least one of PPARr, CEBPa, and FABP4) related to fat metabolism in loin tissue of cattle under heat or cold stress conditions.

In a specific embodiment of the present disclosure, when the cattle were fed with the feed additive composition including NALT as an active ingredient of the present disclosure under cold stress conditions, expression of genes (MYF6, MyoD, and Desmin) related to muscle metabolism in loin tissue of the NALT-treated group did not show a statistically significant difference from expression of the genes related to muscle metabolism in loin tissue of the control, but expression of the genes (PPARr, CEBPa, and FABP4) related to fat metabolism in loin tissue of the NALT-treated group was lower than that of the genes related to fat metabolism in loin tissue of the control (Table 8).

Another object of the present disclosure provides a feed including the feed additive composition for cattle.

Specifically, the feed of the present disclosure may include a feed additive composition for cattle including N-acetyl-L-tryptophan or a salt thereof.

In this regard, descriptions of the "N-acetyl-L-tryptophan", "cattle", "beef cattle", "feed additive", and "rumen-protected" are as provided above.

As used herein, the term "feed" refers to any natural or artificial diet, one meal, or ingredients of the meal that an individual eats, ingests, and digests or which is suitable therefor.

Types of the feed are not particularly limited, and any feeds commonly used in the art may also be used. Non-limiting examples of the feed may include vegetable feeds such as grains, root vegetables, food processing byproducts, algae, fibers, pharmaceutical byproducts, oils, starches, Cucurbitaceae vegetables, or byproducts of grains; and animal feeds such as proteins, inorganic substances, oils and fats, minerals, single-cell proteins, animal planktons, or foods. These feeds may be used alone or in a combination of at least two thereof.

Another aspect of the present disclosure provides a method of reducing temperature stress of cattle, the method including feeding the cattle with a feed additive composition or feed for cattle including N-acetyl-L-tryptophan as an active ingredient. Specifically, provided is a method of reducing temperature stress of beef cattle including a step of feeding the beef cattle with a feed additive composition or feed for beef cattle comprising N-acetyl-L-tryptophan as an active ingredient.

In addition, the method of reducing temperature stress of cattle of the present disclosure may include a step of feeding the cattle with a feed additive composition or feed for cattle including N-acetyl-L-tryptophan or a salt thereof.

Another aspect of the present disclosure provides a method of increasing average daily gain of cattle, the method including feeding the cattle with a feed additive composition or feed for cattle comprising N-acetyl-L-tryptophan as an active ingredient. Specifically, provided is a method of increasing average daily gain of beef cattle including a step of feeding the beef cattle with a feed additive composition or feed for beef cattle including N-acetyl-L-tryptophan as an active ingredient.

In addition, the method of increasing average daily gain of cattle may include a step of feeding the cattle with N-acetyl-L-tryptophan or a salt thereof.

Another aspect of the present disclosure provides a method of increasing feed intake of cattle, the method including feeding the cattle with a feed additive composition or feed for cattle comprising N-acetyl-L-tryptophan as an active ingredient. Specifically, provided is a method of increasing feed intake of beef cattle including a step of feeding the beef cattle with a feed additive composition or feed for beef cattle including N-acetyl-L-tryptophan as an active ingredient.

Also, the method of increasing feed intake of cattle according to the present disclosure may include a step of feeding the cattle with N-acetyl-L-tryptophan or a salt thereof.

In the present disclosure, provided is a method of reducing expression of proteins related to fat metabolism in loin tissue of cattle, the method including feeding the cattle with a feed additive composition or feed for cattle including N-acetyl-L-tryptophan as an active ingredient. Specifically, provided is a method of reducing expression of proteins related to fat metabolism in loin tissue of beef cattle including a step of feeding the beef cattle with a feed additive composition or feed for beef cattle including N-acetyl-L-tryptophan as an active ingredient.

In addition, the method of reducing expression of proteins related to fat metabolism in loin tissue of cattle may include a step of feeding the cattle with a feed additive composition or feed for cattle including N-acetyl-L-tryptophan or a salt thereof.

In this regard, descriptions of the "N-acetyl-L-tryptophan", "beef cattle", "cattle", "feed additive", "rumen-protected", and "feed" are as provided above.

The amount of N-acetyl-L-tryptophan contained in the feed additive composition for cattle is as described above.

These methods may be performed with breeding management technologies well known in the art, and specifically, the feed may be fed at a certain time every day, without being limited thereto. Also, an amount of feed offered is not particularly limited.

MODE OF DISCLOSURE

Hereinafter, the present disclosure will be described in more detail with reference to the following examples. However, the following examples are merely presented to exemplify the present disclosure, and the scope of the present disclosure is not limited thereto.

Efficacy of N-acetyl-L-tryptophan (NALT) when used for cattle, e.g., as a feed for cattle, was identified under heat or cold stress conditions.

A. Identification of Efficacy of NALT Under Cold Stress Conditions

Example 1. Experimental Animal, Experimental Feed, and Experimental Method

Example 1-1. Animal Used for Experiment

In the present disclosure, 8 Korean native steers (8.3±0.72 months old on average) were selected and used.

As shown in Table 2, initial weights of sentinel animals were measured, and the steers were assigned to a control and a NALT-treated group (0.1% NALT), 4 steers each, so as not to show a statistically significant difference therebetween.

TABLE 2

Comparison of initial weight

| Treatments[1] | | | |
|---|---|---|---|
| Control | 0.1% NALT | SEM[2] | p-value |
| 278.5 | 279.7 | 7.69 | 0.9505 |

Example 1-2. Feeding Experimental Feed

Total mixed ration (TMR, Nonghyup Feed Co., Ltd., Yangju-si, Korea) which does not contain antibiotics was fed as a basal diet. Analysis of chemical composition (moisture, crude protein, crude fat, crude ash, etc.) and amino acids (19 types) of the basal diet stored at −20° C. was performed, and the results are shown in Table 3.

TABLE 3

Chemical composition and amino acids of basal diet

| | TMR |
|---|---|
| Chemical composition, % of kg dry matter basis | |
| Dry matter | 86.82 |
| Crude protein | 15.05 |
| Ether extract | 2.49 |
| Crude fiber | 25.90 |
| Crude ash | 6.75 |
| Acid detergent fiber | 32.87 |
| Neutral detergent fiber | 52.26 |
| Amino acids, % of dry matter basis | |
| Tryptophan | 0.09 |
| Methionine | 0.09 |
| Niacin | 0.00 |
| Lysine | 0.54 |
| Aspartic acid | 1.20 |
| Threonine | 0.48 |
| Serine | 0.57 |
| Glutamic acid | 2.04 |
| Glycine | 0.61 |
| Alanine | 0.79 |
| Valine | 0.67 |
| Isoleucine | 0.47 |
| Leucine | 0.97 |
| Tyrosine | 0.29 |
| Phenylalanine | 0.55 |

TABLE 3-continued

Chemical composition and amino acids of basal diet

| | TMR |
|---|---|
| Histidine | 0.29 |
| Arginine | 0.71 |
| Cystine | 0.12 |
| Proline | 0.91 |

Example 1-3. Designing Experimental Method and Statistical Analysis

After grouping the animals by statistical analysis of initial body weights, the animals were bred in 1.0×1.5 m² individual pens during the experiment period. The feed was offered based on an amount of dry matter of daily total mixed ration (TMR) per head. After 7 days of an adaptation period for N-acetyl-L-tryptophan (NALT), a mixture of 0.1% N-acetyl-L-tryptophan (NALT) and the total mixed ration was fed to individual animals every morning at 8 a.m. for 6 weeks, and water was available ad libitum. Total amounts of L-tryptophan ingested by the control and NALT-treated group by feeding NALT were 7.37 g/day/head and 16.26 g/day/head, respectively. The experiment was performed such that the NALT-treated group ingested 8.89 g/day/head more L-tryptophan than that of the control.

Meanwhile, results of growth performance analysis (body weight and average feed intake) and genetic analysis of loin tissue were obtained by statistically comparing and analyzing significant differences between the control and the NALT-treated group, and results of hematological analysis were obtained via statistical comparison and analysis depending on NALT treatment, experiment period (days), and interaction (treatment×days). These numerical values were expressed as average values, and a significance test was performed at the 5% level using Student's t-test by using the JMP 5.0 software package (SAS Institute Inc., Cary, NC, USA).

Example 2. Analysis of Temperature and Relative Humidity

Temperature (° C.) and relative humidity (%) were recorded every day during a one-week adaptation period and a 6-week experiment period using a portable temperature and humidity meter. Average temperature and average relative humidity of each week were calculated using the temperature and relative humidity recorded during the total experiment period.

Changes in the average temperature and average relative humidity are as shown in Table 4. An average temperature during the adaptation period (days 0-6) was 4.3° C., and average temperatures during the experiment period were in the range of −6.2° C. to 4.2° C., relatively low compared to that of the adaptation period. In addition, an average temperature of the entire experiment period (days 7-48) was −1.0° C.

TABLE 4

Changes in average temperature and average relative humidity during entire experiment period

| Period | $Temp_{avg}$, ° C. | SEM | $RH_{avg}$, % | SEM |
|---|---|---|---|---|
| Days 0-6 | 4.3 | 1.48 | 69.9 | 5.75 |
| Days 7-13 | −6.2 | 1.74 | 48.8 | 4.34 |
| Days 14-20 | −2.5 | 1.21 | 49.4 | 2.11 |

TABLE 4-continued

Changes in average temperature and average relative humidity during entire experiment period

| Period | Temp$_{avg}$, °C. | SEM | RH$_{avg}$, % | SEM |
|---|---|---|---|---|
| Days 21-27 | −3.5 | 1.05 | 45.0 | 1.32 |
| Days 28-34 | 0.3 | 1.16 | 50.8 | 4.45 |
| Days 35-41 | 2.3 | 1.27 | 50.3 | 4.79 |
| Days 42-48 | 4.2 | 0.36 | 55.7 | 5.59 |
| Days 7-48 | −1.0 | 0.73 | 49.9 | 1.59 |

Example 3. Analysis of Body Weight

Initial weight (day 0), intermediate weight (day 27), and end weight (day 48) of sentinel animals were measured, i.e., three times in total, before offering morning feed. The average daily gain (average daily weight gain, ADG) of the sentinel animals was calculated by dividing the differences in weight, between the initial weight and the intermediate weight and between the intermediate weight and the end weight, by the total number of days of the experiment.

Analysis results of changes in body weight of the control and the NALT-treated group are as shown in Table 5. As a result of measuring changes in body weight of the sentinel animals at the mid-point of the experiment (day 27) and the final day of the experiment (day 48), no statistically significant difference was observed between the total weight change of the NALT-treated group and that of the control. However, as a result of comparing the average daily gain (ADG) from the starting day of the experiment (day 0) to the mid-point of the experiment (day 27) with the average daily gain (ADG) from the mid-point of the experiment (day 27) to the final day of the experiment (day 48), statistically significant differences were observed in the average daily gain (ADG) of 0.753 (p=0.0301) and 0.766 (p=0.0003) in the NALT-treated group when compared with the control (not treated with NALT). In addition, as a result of comparing feed conversion ratios (FCR) during the same experiment period, it was confirmed that the control and the NALT-treated group had feed conversion ratios (FCR) of 13.3 (p=0.035) and 4.82 (p<0.001), respectively, indicating that feed efficiency was increased by supplying NALT. This indicates that feed efficiency of the NALT-treated group was increased compared to that of the control since the feed conversion ratio of the NALT-treated group was 37%, decreased by 63% compared to the control. (The feed conversion ratio is a value obtained by dividing average daily gain by feed intake, and a lower feed conversion ratio indicates a higher feed efficiency.)

TABLE 5

Change in body weight according to NALT feeding

| | Control | NALT | SEM | p-value |
|---|---|---|---|---|
| Day 0 | | | | |
| Body weight, kg | 278.5 | 279.7 | 7.69 | 0.950 |
| Day 27 | | | | |
| Body weight, kg | 285.1 | 301.5 | 8.30 | 0.360 |
| ADG, kg/day | 0.224 | 0.753 | 0.130 | 0.030 |
| Feed conversion ratio[5] | 44.4 | 13.3 | 13.25 | 0.035 |
| Day 48 | | | | |
| Body weight, kg | 290.9 | 315.7 | 4.72 | 0.194 |
| ADG, kg/day | 0.262 | 0.766 | 0.1 | <0.001 |
| Feed conversion ratio | 13.03 | 4.82 | 1.18 | <0.001 |

Example 4. Analysis of Feed Intake

Feed intake of each sentinel animal was calculated by measuring a total amount of feed offered and an amount left over every day.

Analysis results of changes in feed intake of the control and the NALT-treated group are as shown in Table 6. No statistically significant difference (p=0.0883) was observed between the feed intake of the NALT-treated group during the adaptation period (days 0-6) and the feed intake of the control during the adaptation period. In addition, although no statistically significant difference was observed between the feed intake of the NALT-treated group during the experiment period of days 7-41 and the feed intake of the control during the same experiment period, a statistically significant difference (p=0.0384) was observed between the feed intake of the NALT-treated group during the experiment period of days 42-48, which was increased by about 1.02 kg, compared with the feed intake of the control during the same experiment period. In addition, as a result of calculating average feed intake per head during the entire experiment period (days 7-48), average feed intake (9.86 kg/day/head) of the NALT-treated group was increased compared to the average feed intake (9.43 kg/day/head) of the control by about 4.6% (p=0.0119), indicating a statistically significant difference.

TABLE 6

Change in feed intake according to NALT feeding Treatments[1]

| Period | Control | 0.1% NALT | SEM[2] | p-value |
|---|---|---|---|---|
| | kg of feed intake | | | |
| Days 0-6 | 8.93 | 8.56 | 0.108 | 0.0883 |
| Days 7-13 | 9.24 | 9.21 | 1.647 | 0.9483 |
| Days 14-20 | 9.41 | 9.56 | 1.171 | 0.6232 |
| Days 21-27 | 9.60 | 9.68 | 1.200 | 0.7910 |
| Days 28-34 | 9.68 | 10.22 | 1.557 | 0.2013 |
| Days 35-41 | 9.15 | 10.02 | 1.743 | 0.0632 |
| Days 42-48 | 9.54 | 10.56 | 1.725 | 0.0384 |
| Days 7-48 | 9.43 | 9.86 | 1.533 | 0.0119 |

Example 5. Hematological Analysis

Blood was collected from a jugular vein of each sentinel animal before offering the feed at the starting day of the experiment (week 0), the mid-point of the experiment (week 4), and the final day of the experiment (week 7) and added to a vacutainer (Becton Dickinson, Franklin Lakes, NJ, USA). Hematological analysis was conducted using a VetScan HM2 Hematology System (Abaxis, Union City, CA, USA).

Hematological analysis results of the control and the NALT-treated group are as shown in Table 7. No statistically significant difference between the control and the NALT-treated group was observed in all hematological indicators except for monocytes, and all values were found to be within normal ranges.

TABLE 7

Change in hematological properties according to NALT feeding

| | Treatments[1] | | | | | | | p-value | | |
| --- | --- | --- | --- | --- | --- | --- | --- | --- | --- | --- |
| | Control | | | 0.1% NALT | | | | | | |
| | 0 wks | 4 wks | 7 wks | 0 wks | 4 wks | 7 wks | SEM[2] | treatment (T) | days (D) | T × D |
| WBC3 | 9.28 | 9.44 | 8.92 | 8.66 | 8.70 | 9.34 | 0.335 | 0.6815 | 0.9841 | 0.7830 |
| LYM | 6.07 | 6.25 | 5.26 | 5.55 | 6.55 | 5.98 | 0.234 | 0.7329 | 0.5086 | 0.3023 |
| MON | 0.24 | 0.24 | 0.23 | 0.10 | 0.06 | 0.08 | 0.043 | 0.0047 | 0.0002 | 0.0019 |
| GRA | 2.98 | 2.94 | 3.44 | 3.01 | 2.09 | 3.29 | 0.214 | 0.4665 | 0.3074 | 0.4322 |
| RBC | 10.33 | 9.97 | 9.00 | 10.70 | 10.34 | 10.08 | 0.266 | 0.2118 | 0.2050 | 0.6769 |
| HGB | 13.33 | 13.73 | 12.65 | 13.60 | 14.20 | 13.68 | 0.237 | 0.2449 | 0.9520 | 0.4339 |
| HCT | 34.57 | 34.12 | 31.66 | 35.00 | 34.64 | 33.88 | 0.584 | 0.3946 | 0.3787 | 0.7956 |
| MCH | 13.03 | 13.85 | 14.10 | 12.83 | 13.80 | 13.70 | 0.248 | 0.6806 | 0.2577 | 0.9625 |
| PLT | 398.5 | 455.8 | 367.5 | 378.0 | 476.8 | 379.5 | 15.389 | 0.8862 | 0.0360 | 0.8263 |

Example 6. Analysis of Gene Expression Related to Loin Tissue Development

Samples of loin tissue of the sentinel animals were obtained at the final day of the experiment (day 48) using a biopsy gun for large animals (TNT Research Co., Ltd., Gyeonggi-do, Republic of Korea), added to a 2 mL tube, and incubated in liquid nitrogen gas. After extracting RNA from each tissue sample, real-time PCR was conducted to analyze expression levels of genes related to muscle metabolism (MYF6, MyoD, and Desmin) and fat metabolism (PPARr, CEBPa, and FABP4) of the loin tissue of each animal.

Results of analysis of gene expression related to loin tissue development of the control and the NALT-treated group are as shown in Table 8. No statistically significant difference was observed between the expression of the genes (MYF6, MyoD, and Desmin) related to muscle metabolism of loin tissue of the NALT-treated group and the expression of the genes related to muscle metabolism of loin tissue of the control. However, the expression levels of the genes (PPARr, CEBPa, and FABP4) related to fat metabolism of loin tissue of the NALT-treated group were lower than those of the fat metabolism—related genes in the loin tissue of the control. It is considered that L-tryptophan supplemented via NALT inhibited fat metabolism under cold stress conditions, and thus energy previously required for the fat metabolism is used in maintaining and improving homeostasis in the body (body temperature and the like), and therefore average daily gain and feed conversion ratios were increased thereby.

TABLE 8

Expression levels of genes related to muscle metabolism and fat metabolism of loin tissue according to NALT feeding

| | Treatments[1] | | | |
| --- | --- | --- | --- | --- |
| | Control | 0.1% NALT | SEM[2] | p-value |
| PPARr | 1.000 | 0.274 | 0.2302 | <0.000 |
| CEBPa | 1.000 | 0.293 | 0.2714 | <0.000 |
| FABP4 | 1.000 | 0.233 | 0.2618 | <0.000 |
| MYF6 | 1.000 | 0.834 | 0.1667 | 0.071 |
| MyoD | 1.000 | 0.857 | 0.1822 | 0.676 |
| Desmin | 1.000 | 0.871 | 0.1902 | 0.140 |

B. Identification of Efficacy of NALT Under Heat Stress Conditions

Example 1. Experimental Animal, Experimental Feed, and Experimental Method

Example 1-1. Animal Used in Experiment

In the present disclosure, 8 Korean native steers (15.9±0.16 months old on average) were selected and used. The experimental procedure and method were approved by the Institutional Animal Care and Use Committee at Konkuk University, Seoul, Republic of Korea (Approval No. KU17136).

As shown in Table 9, initial weights of sentinel animals were measured, and the steers were assigned to a control and a NALT-treated group (0.1% NALT), 4 steers each, so as not to show a statistically significant difference therebetween.

TABLE 9

Comparison of initial weight

| Treatments | | | |
| --- | --- | --- | --- |
| Control | 0.1% NALT | SEM | p-value |
| 420.5 | 428.8 | 14.91 | 0.8058 |

Example 1-2. Feeding Experimental Feed

Total mixed ration (TMR, Nonghyup Feed Co., Ltd., Yangju-si, Korea) which does not contain antibiotics was fed as a basal diet. Analysis of chemical composition (moisture, crude protein, crude fat, crude ash, etc.) and amino acids (19 types) of the basal diet stored at −20° C. was performed, and the results are shown in Table 3.

Example 1-3. Designing of Experimental Method and Statistical Analysis

After grouping the animals by statistical analysis of initial body weights, the animals were bred in 1.0×1.5 m² individual pens during the experiment period. The feed was offered based on an amount of dry matter of daily total mixed ration (TMR) per head. After 7 days of an adaptation period for N-acetyl-L-tryptophan (NALT), a mixture of 0.1% N-acetyl-L-tryptophan (NALT) and the total mixed ration was fed to individual animals every morning at 8 a.m. for 6 weeks, and water was available ad libitum. Total amounts of L-tryptophan ingested by the control and the experimental group (NALT-treated group) by feeding NALT were 6.0 g/day/head and 18.2 g/day/head, respectively. The experiment was performed such that the NALT-treated group ingested 12.2 g/day/head more L-tryptophan than the control.

Meanwhile, results of growth performance analysis (body weight and average feed intake) and genetic analysis of loin tissue were obtained by statistically comparing and analyzing significant differences between the control and the NALT-treated group, and results of hematological analysis were obtained via statistical comparison and analysis depending on NALT treatment, experiment period (days), and interaction (treatment×days). These numerical values were expressed as average values, and a significance test was performed at the 5% level using Student's t-test by using a JMP 5.0 software package (SAS Institute Inc., Cary, NC, USA).

Example 2. Analysis of Temperature and Relative Humidity

Temperature (° C.) and relative humidity (%) were recorded every day during a one-week adaptation period and a 6-week experiment period using a portable temperature and humidity meter. Average temperature and average relative humidity of each week were calculated using the temperature and relative humidity recorded during the total experiment period. In addition, a temperature-humidity index (THI) was calculated using temperature and humidity as shown in the following equation, and heat stress state may be diagnosed using the THI as an index feature of a heat load.

$$THI=(1.8 \times T+32)-[0.55-0.0055 \times RH] \times (1.8 \times T-26.8)$$

In this regard, T is a maximum temperature (° C.) of the region, and RH is average relative humidity (%) on the day of a test.

Changes in average temperature, maximum temperature, relative humidity, and THI are as shown in Table 10. The average THI was over 80 during the first 3 weeks, and the average THI was over 72 during the next 4 weeks.

TABLE 10

Average temperature, maximum temperature, average relative humidity, and THI during entire experiment period

| Period | $Temp_{avg}$, ° C. | $Temp_{max}$, ° C. | $RH_{avg}$, % | THI |
|---|---|---|---|---|
| Day 0 | 34.6 | 45.3 | 62.5 | 85.0 |
| Week 1 | 32.8 | 41.7 | 62.0 | 84.8 |
| Week 2 | 41.3 | 58.4 | 54.1 | 84.3 |
| Week 3 | 30.3 | 42.4 | 59.8 | 80.3 |
| Week 4 | 29.6 | 40.1 | 64.9 | 77.8 |
| Week 5 | 29.5 | 37.7 | 71.1 | 76.6 |
| Week 6 | 22.4 | 32.2 | 59.9 | 72.1 |
| Week 7 | 21.8 | 30.7 | 65.6 | 72.2 |
| Week 8 | 20.7 | 30.7 | 63.7 | 68.3 |
| Week 9 | 19.1 | 29.6 | 62.7 | 65.3 |
| Week 10 | 16.8 | 24.7 | 65.9 | 62.0 |
| Average | 27.1 | 37.6 | 62.9 | 75.3 |

Example 3. Analysis of Body Weight

Initial weight (week 0), intermediate weight (week 5), and end weight (week 10) of sentinel animals were measured, i.e., three times in total, before offering morning feed. The average daily gain (ADG) of the sentinel animals was calculated by dividing the differences in weight, between the initial weight and the intermediate weight and between the intermediate weight and the end weight, by the total number of days of the experiment.

Analysis results of changes in body weight of the control and the NALT-treated group are as shown in Table 11. As a result of measuring changes in body weight of the sentinel animals at the mid-point of the experiment (week 5) and the final day of the experiment (week 10), increases in average daily gain (ADG) were observed in the NALT-treated group compared to the control. In particular, the average daily gain of the NALT-treated group was significantly increased when compared to the average daily gain of the control during the period where the THI was over 80, i.e., under high heat stress conditions.

TABLE 11

Change in body weight according to NALT feeding

| | Treatments | | |
|---|---|---|---|
| | Control | 0.1% NALT | SEM |
| Week 0, kg | 420.5 | 428.8 | 14.91 |
| Week 5, kg | 457.0 | 480.8 | 18.84 |
| ADG, kg/days | 1.04 | 1.49 | 0.19 |
| Week 10, kg | 493.8 | 510.5 | 17.93 |
| ADG, kg/days | 1.05 | 0.85 | 0.05 |
| Total ADG, kg/d | 1.05 | 1.17 | 0.12 |

Example 4. Analysis of Feed Intake and Drinking Water Intake

Feed intake of each sentinel animal was calculated by measuring a total amount of feed offered and an amount left over every day, and drinking water intake thereof was calculated every day by measuring a total amount of drinking water offered and an amount left over. Also, since the amount of feed left over was measured in pen units, DMI/BW % was calculated using the equation DMI/BW %=1.2425+1.9218×NEm−0.7259×(NEm)² and corrected using actual data of the experiment to calculate data for each of the two heads included in each pen. Analysis results of changes in feed intake and drinking water intake of the control and the NALT-treated group are shown in Table 12. No statistically significant difference was observed between average feed intake (13.38 kg/day) of the control and average feed intake (13.62 kg/day) of the NALT-treated group during the entire experiment period. However, when the THI was over 80, the feed intake of the NALT-treated group was significantly increased compared with that of the control by 0.8 kg (6.23%). In contrast, the drinking water intake of the NALT-treated group exhibited a statistically significant decrease regardless of THI conditions. Based thereon, it may be interpreted that the feed intake of cattle fed with NALT increased compared with the control without having increased drinking water intake even under heat stress conditions.

TABLE 12

Change in feed intake and drinking water intake according to NALT feeding (relative to THI 80)

| $THI_{avg} > 80$ | | | | $THI_{avg} < 80$ | | | |
|---|---|---|---|---|---|---|---|
| Control | 0.1% NALT | SEM | p-value | Control | 0.1% NALT | SEM | p-value |
| Feed intake, kg | | | | | | | |
| 12.7 | 13.5 | 0.33 | 0.0096 | 13.8 | 13.7 | 0.2 | 0.6240 |
| Drinking water intake, kg | | | | | | | |
| 55.0 | 44.6 | 2.15 | <0.0001 | 47.1 | 35.3 | 1.73 | <0.0001 |

Example 5. Analysis of Blood

Blood samples were collected from a jugular vein of each sentinel animal before offering the feed at the starting day of the experiment (week 0), the mid-point of the experiment (week 5), and the final day of the experiment (week 10) and stored in a vacutainer (Becton Dickinson, Franklin Lakes, NJ, USA). Complete blood cell count (CBC) was performed using whole blood using a VetScan HM2 (Abaxis, Union City, CA, USA), and hematological properties were identified using serum with a biochemical autoanalyzer (FUJI DRI-CHEM 7000, Fujifilm, Tokyo, Japan). In addition, total protein (TP), albumin (ALB), creatinine phosphokinase (CPK), and blood urea nitrogen (BUN), which are related to blood protein metabolism, were analyzed; triglycerides (TG) and non-esterified fatty acid (NEFA), which are related to energy metabolism, were analyzed; and sodium (Na), chlorine (Cl), and potassium (K), which are blood electrolytes, were analyzed.

Results of CBC analysis of the control and the NALT-treated group are as shown below (Table 13). No statistically significant difference was observed in all CBC test indicators by treatment with 0.1% NALT. Although RBC, HGB, MCV, MCH, and GRA showed significant differences according to dates of sampling, it was confirmed that all values of hematological indicators were within normal ranges.

TABLE 13

CBC analysis according to NALT feeding

| | Treatments | | | | | | SEM | p-value | | |
|---|---|---|---|---|---|---|---|---|---|---|
| | Control | | | 0.1% NALT | | | | | | |
| Item | Day 0 | Day 35 | Day 70 | Day 0 | Day 35 | Day 70 | $SEM^2$ $SEM^2$ | TRT (T) | Days (D) | T × D |
| RBC (5.0-10.0, $10^6/\mu L$) | 7.92 | 9.25 | 8.71 | 9.13 | 8.04 | 8.83 | 0.42 | 0.216 | 0.019 | 0.112 |
| HGB 8.0-15.0, g/dL | 12.4 | 14.0 | 13.2 | 13.4 | 11.7 | 13.8 | 0.38 | 0.025 | 0.002 | 0.058 |
| MCV (40-60, fL) | 42.8 | 41.3 | 42.0 | 38.8 | 40.0 | 42.5 | 2.07 | 0.826 | <0.001 | 0.564 |
| MCHC (30-36, g/dL) | 36.7 | 37.1 | 36.5 | 38.3 | 37.1 | 37.1 | 0.55 | 0.209 | 0.504 | 0.668 |
| HCT (23-33, %) | 8.10 | 6.80 | 6.98 | 6.95 | 6.58 | 9.80 | 6.46 | 0.298 | 0.053 | 0.372 |
| MCH (14-18, pg) | 15.7 | 15.3 | 15.3 | 14.8 | 14.7 | 15.7 | 0.71 | 0.994 | 0.026 | 0.873 |
| RDW (16-20, %) | 24.5 | 23.0 | 23.5 | 23.6 | 22.7 | 23.6 | 0.71 | 0.892 | 0.135 | 0.248 |
| PLT (100-800, $10^3/\mu L$) | 302 | 436 | 413 | 332 | 371 | 196 | 47.6 | 0.362 | 0.053 | 0.501 |
| MPV (4.5-7.6, fL) | 8.10 | 6.80 | 6.98 | 6.95 | 6.58 | 9.80 | 6.46 | 0.298 | 0.053 | 0.372 |
| PCT (0.15-0.40, %) | 0.25 | 0.31 | 0.29 | 0.24 | 0.24 | 0.24 | 0.06 | 0.988 | 0.194 | 0.933 |
| PDW (56-80, %) | 36.2 | 34.2 | 32.4 | 34.1 | 31.5 | 29.5 | 2.26 | 0.730 | 0.812 | 0.352 |
| WBC (4.0-12.0, $10^3/\mu L$) | 9.76 | 10.4 | 11.3 | 9.60 | 9.74 | 9.38 | 0.98 | 0.732 | 0.175 | 0.815 |
| LYM (2.5-7.5, $10^3/\mu L$) | 4.80 | 6.56 | 6.29 | 6.08 | 5.67 | 4.91 | 0.69 | 0.742 | 0145 | 0.946 |
| MON (0-0.84, $10^3/\mu L$) | 0.58 | 0.43 | 0.83 | 0.22 | 0.46 | 0.81 | 0.21 | 0.575 | 0.323 | 0.259 |
| GRA (0-2.4, $10^3/\mu L$) | 4.38 | 3.37 | 4.20 | 3.16 | 3.61 | 3.66 | 0.66 | 0.450 | 0.008 | 0.167 |

Results of hematological analysis of the control and the NALT-treated group are as shown below (Table 14). No statistically significant difference was observed in all CBC test indicators by treatment with 0.1% NALT, and TP, ALB, BUN, GLU, Na, and CI are shown below.

control. It is considered that the supplemented NALT not only promoted lipolysis but also promoted metabolism of transporting degraded fat and genes related to muscle metabolism under heat stress conditions, and thus average daily gain increased (Table 11).

TABLE 14

Change in hematological properties according to NALT feeding

| Item | Control Day 0 | Control Day 35 | Control Day 70 | 0.1% NALT Day 0 | 0.1% NALT Day 35 | 0.1% NALT Day 70 | SEM $SEM^2$ $SEM^2$ | p-value TRT (T) | p-value Days (D) | T × D |
|---|---|---|---|---|---|---|---|---|---|---|
| TP | 6.0 | 6.4 | 6.2 | 6.1 | 6.5 | 6.3 | 0.13 | 0.558 | 0.010 | 0.852 |
| ALB | 3.1 | 3.3 | 3.4 | 3.3 | 3.6 | 3.5 | 0.10 | 0.224 | <0.001 | 0.330 |
| GLO | 2.9 | 3.1 | 2.9 | 2.8 | 2.9 | 2.9 | 0.07 | 0.319 | 0.129 | 0.471 |
| CPK | 150 | 144 | 189 | 112 | 267 | 276 | 60.9 | 0.264 | 0.075 | 0.163 |
| BUN | 18.2 | 19.0 | 21.7 | 16.7 | 19.8 | 18.5 | 1.08 | 0.421 | 0.006 | 0.031 |
| GLU | 49.5 | 42.8 | 52.6 | 49.6 | 39.1 | 56.3 | 2.29 | 0.928 | 0.009 | 0.356 |
| NEFA | 178 | 177 | 137 | 139 | 167 | 168 | 12.6 | 0.684 | 0.387 | 0.019 |
| TG | 21.0 | 18.5 | 22.4 | 25.5 | 19.1 | 22.1 | 4.15 | 0.721 | 0.383 | 0.893 |
| Na | 141.4 | 141.4 | 141.5 | 141.3 | 142.6 | 141.1 | 0.31 | 0.598 | 0.029 | 0.027 |
| K | 4.7 | 4.5 | 4.7 | 4.7 | 4.8 | 4.9 | 0.16 | 0.321 | 0.482 | 0.710 |
| Cl | 102.5 | 100.1 | 102.8 | 102.3 | 101.4 | 103.0 | 0.43 | 0.458 | 0.009 | 0.290 |

TP: Total protein; ALB: Albumin; GLO: globulin (=TP − ALB); CPK: creatinine phosphokinase; BUN: blood urea nitrogen; GLU: glucose; NEFA: non-esterified fatty acid; TG: triglyceride; Na: sodium; K: potassium; and Cl: chlorine

Example 6. Analysis of Gene Expression Related to Loin Tissue Development

Samples of loin tissue of the sentinel animals were obtained on the final day of the experiment (week 10). The samples were obtained using a biopsy gun for animals (TNT Research Co., Ltd., Gyeonggi-do, Republic of Korea), added to a 2 mL tube, and incubated in liquid nitrogen gas. After extraction of RNA from each tissue sample, real-time PCR was conducted to analyze expression levels of genes related to fat differentiation (PPARr, CEBPa, FABP4, LPL, and SCD) and muscle differentiation (MYF6, MyoD, and MyoG) of the loin tissue of each animal. Total RNA was isolated using the TRIzol RNA isolation protocol, and the amount of RNA was measured using a NanoDrop 1000 (Thermo Scientific, Seoul, Republic of Korea). The RNA integrity (RIN) was estimated using an RNA Nano 6000 Assay Kit of the Agilent Bioanalyzer 2100 system (Agilent Technologies, Richardson, USA), and an obtained RNA integrity number (RIN) was 6.5±0.27. After synthesizing cDNA from mRNA, real-time PCR was conducted to measure expression levels of the genes.

Analysis results of gene expression related to loin tissue development of the control and the NALT-treated group are as shown below (Table 15). No statistically significant difference was observed in the expression of the muscle differentiation-related gene (MyoD) and the fat differentiation-related genes (C/EBPα and PPARγ) by treatment with 0.1% NALT compared to the control (p>0.05). However, the expression levels of the muscle differentiation-related genes (MYF6 and MyoG) and genes related to lipolysis and transport of fat (FABP4 and LPL) in loin tissue of the 0.1% NALT-treated group were higher than those of the control (p<0.05), and the gene expression level of SCD in the 0.1% NALT-treated group tended to be higher than that of the

TABLE 15

Expression levels of genes related to muscle metabolism and fat metabolism of loin tissue according to NALT feeding

| Gene | Treatments Control | Treatments 0.1% NALT | SEM $SEM^2$ | p-value p-value |
|---|---|---|---|---|
| C/EBPα | 1.00000 | 0.80533 | 0.185 | 0.279 |
| FABP4 | 1.00000 | 1.50083 | 0.227 | 0.031 |
| LPL | 1.00000 | 1.77365 | 0.177 | 0.014 |
| MyoD | 1.00000 | 1.04500 | 0.189 | 0.229 |
| MYF6 | 1.00000 | 1.09295 | 0.175 | 0.006 |
| MyoG | 1.00000 | 2.08629 | 0.311 | <0.001 |
| PPARγ | 1.00000 | 1.30108 | 0.359 | 0.199 |
| SCD | 1.00000 | 1.44823 | 0.233 | 0.086 |

The above description of the present disclosure is provided for the purpose of illustration, and it would be understood by those skilled in the art that various changes and modifications may be made without changing the technical conception and essential features of the present disclosure. Thus, it is clear that the above-described embodiments are illustrative in all aspects and do not limit the present disclosure. The various embodiments disclosed herein are not intended to be limiting, with the true scope and spirit being indicated by the following claims. The present disclosure is to be limited only by the terms of the appended claims, along with the full scope of equivalents to which such claims are entitled.

The invention claimed is:
1. A method of reducing temperature stress of cattle, the method comprising:
 feeding the cattle with a feed additive composition or a feed for cattle comprising N-acetyl-L-tryptophan as an active ingredient, and breeding the cattle under a temperature stress condition, thereby increasing average daily gain and feed intake of the cattle compared to a control cattle not treated with N-acetyl-L-tryptophan.

2. The method of claim 1, wherein the temperature stress is cold stress or heat stress.

3. The method of claim 2, wherein the cold stress is stress caused at a temperature of 10° C. or lower.

4. The method of claim 2, wherein the heat stress is stress caused at a temperature of 15° C. or higher.

5. The method of claim 1, wherein the N-acetyl-L-tryptophan is comprised in an amount of 0.01% (w/w) to 3.0% (w/w) based on a total dry weight of a feed.

* * * * *